United States Patent [19]
Gatto et al.

[11] Patent Number: 6,001,786
[45] Date of Patent: Dec. 14, 1999

[54] SULFURIZED PHENOLIC ANTIOXIDANT COMPOSITION METHOD OF PREPARING SAME AND PETROLEUM PRODUCTS CONTAINING SAME

[75] Inventors: Vincent James Gatto, Midlothian, Va.; Abbas Kadkhodayan, Collinsville, Ill.

[73] Assignee: Ethyl Corporation, Richmond, Va.

[21] Appl. No.: 08/877,533

[22] Filed: Feb. 19, 1997

[51] Int. Cl.[6] .......................... C10M 135/30; C10L 1/24
[52] U.S. Cl. ................... 508/570; 508/572; 508/573; 44/435; 252/404; 252/406
[58] Field of Search .................. 508/572, 573, 508/570; 44/435

[56] References Cited

U.S. PATENT DOCUMENTS

| | | | |
|---|---|---|---|
| 3,250,712 | 5/1966 | Coffield | 252/48.2 |
| 3,326,800 | 6/1967 | Coffield | 44/435 |
| 3,678,115 | 7/1972 | Fujisawa et al. | 260/609 F |
| 3,718,699 | 2/1973 | Fujisawa et al. | 260/608 |
| 3,835,196 | 9/1974 | Fujisawa et al. | 260/608 |
| 3,929,654 | 12/1975 | Brewster et al. | 252/48.2 |
| 4,551,259 | 11/1985 | Braid | 508/571 |
| 4,740,578 | 4/1988 | Onoe et al. | 568/62 |
| 4,877,902 | 10/1989 | Gatto | 568/23 |
| 4,946,610 | 8/1990 | Lam et al. | 252/48.2 |
| 5,004,481 | 4/1991 | Lam et al. | 44/435 |
| 5,045,089 | 9/1991 | Lam et al. | 44/435 |
| 5,166,439 | 11/1992 | Lam et al. | 564/384 |
| 5,319,144 | 6/1994 | Chiu | 568/23 |
| 5,376,290 | 12/1994 | Meier et al. | 252/47.5 |
| 5,427,701 | 6/1995 | Meier et al. | 252/47.5 |
| 5,516,441 | 5/1996 | Denis | 508/571 |
| 5,520,709 | 5/1996 | Wei et al. | 44/435 |

FOREIGN PATENT DOCUMENTS

| | | |
|---|---|---|
| 430527-A1 | 6/1991 | European Pat. Off. . |
| 432933-A1 | 6/1991 | European Pat. Off. . |
| 811631-A2 | 12/1997 | European Pat. Off. . |
| 1290132 | 9/1972 | United Kingdom . |
| 93/06195 | 4/1993 | WIPO . |
| 97/24417 | 7/1997 | WIPO . |

OTHER PUBLICATIONS

*Synthesis*, Nov., 1972, pp. 624–625.
*Synthesis*, Jan., 1973, pp. 38–39.

*Primary Examiner*—Ellen M. McAvoy
*Attorney, Agent, or Firm*—Dennis H. Rainear; Thomas Hamilton

[57] ABSTRACT

The present invention relates generally to substantially liquid, chlorine-free, sulfur-bridged phenols useful as antioxidants and more specifically to the preparation of a substantially liquid, chlorine-free, sulfur-bridged, hindered phenol compositions, using 1-propanol as the reaction solvent, which are effective antioxidant(s) in lubricating oils and liquid organic fuels without causing excessive copper corrosion and which exhibit improved elastomer seal compatibility. The invention also includes lubricating oils and liquid organic fuels containing an antioxidant additive of the present invention, as well as a method of reducing oxidation in the lubricating oil or liquid organic fuel used in a machine such as an internal combustion engine.

30 Claims, No Drawings

SULFURIZED PHENOLIC ANTIOXIDANT COMPOSITION METHOD OF PREPARING SAME AND PETROLEUM PRODUCTS CONTAINING SAME

TECHNICAL FIELD

The present invention is directed to the use of 1-propanol as a solvent in the reaction of hindered phenols with sulfur. The use of 1-propanol as a solvent in the reaction of hindered phenols with sulfur is unique in that a product high in oligomer content is produced. The advantages of high oligomer contents are lower volatility, improved oil solubility, and the ability to produce a liquid product having a low sulfur content. The antioxidant compositions of the present invention exhibit excellent elastomer seal compatibility and improved corrosion properties.

BACKGROUND

In providing lubricants for internal combustion engines, such as those used in passenger cars and trucks, it is desirable to provide antioxidant additives that improve the useful life of the lubricants and reduce engine corrosion.

Antioxidants in the form of hindered, sulfur-bridged phenols having a branched alkyl group on the alpha carbon atom and made by reacting the phenol with sulfur dichloride in a solvent with recovery of a crystalline product from the reaction mixture are disclosed in U.S. Pat. No. 3,250,712.

The preparation of a crystalline 4,4-thiobis-(2,6-di-t-butylphenol) product by reacting the phenol with a sulfur halide in a solvent such as acetonitrile, carbon disulfide or carbon tetrachloride with or without a catalyst followed by treating the reaction mixture with alkali hydroxide in alcohol is disclosed in U.S. Pat. No. 3,678,115.

The preparation of a liquid lubricant oil additive mixture of 45–75 wt % ortho-alkylphenol and certain amounts of mono-, di-, tri- and tetrasulfides of the phenol by the reaction of an excess of the phenol with sulfur using an organic amine catalyst is disclosed in U.S. Pat. No. 3,929,654. It is also reported in this patent that sulfurized alkylphenols prepared by reacting an alkylphenol with sulfur mono- or dichloride tend to cause copper corrosion probably due to the presence of corrosive sulfur species such as sulphochlorinated alkylphenol.

U.S. Pat. No. 4,946,610 discloses a liquid, sulfur-bridged, hindered phenol antioxidant composition that is prepared by reacting a mixture of hindered phenols with a sulfur chloride in the presence of a polar modifier. The composition is an effective antioxidant in lubricating oils without causing excessive copper corrosion.

Co-pending application, Ser. No. 08/657,141, filed Jun. 3, 1996, relates to the preparation of sulfurized t-butylphenol oligomers using solvents analogous and homologous to 1-propanol, e.g., ethanol, 2-propanol, 1-butanol, and isobutyl alcohol. The products taught in Ser. No. 08/657,141 have less oligomeric products than the products of the present invention.

One of the objects of this invention is the preparation of an oil soluble, chlorine-free, sulfurized hindered phenolic antioxidant that is compatible with elastomer seals, does not cause excessive copper corrosion and is a highly effective antioxidant in low phosphorus (<1000 ppm phosphorus) lubricating oils used primarily in passenger cars and trucks.

SUMMARY OF THE INVENTION

This invention relates generally to substantially liquid, chlorine-free, sulfur-bridged phenols useful as antioxidants and more specifically to the preparation of substantially liquid, chlorine-free, sulfur-bridged, hindered phenol compositions which are effective antioxidant(s) in lubricating oils and liquid organic fuels without damaging elastomer seals and causing excessive copper corrosion. The invention also includes lubricating oils and liquid organic fuels containing the hindered thiophenol antioxidant additive of the present invention, as well as a method of reducing oxidation in the lubricating oil and liquid organic fuel used in a machine such as an internal combustion engine.

As used herein, reference to substantially liquid character refers to compositions that are chiefly liquid. In this regard, aged samples of prior substantially liquid, chlorine-free, sulfur-bridged phenols do tend to form a slight amount of crystallization, generally around the sides of a container where product comes in contact with air and the glass container surface. Sometimes more substantial crystallization is seen as a slight sediment at the bottom of the sample. Generally the amount of crystallization is small but increases significantly with a small drop in sulfur content. For example, the hindered phenols of Ser. No. 08/657,141 prepared with 0.43 parts of sulfur/1 part hindered phenol generally has only slight crystallization from aged samples at room temperature. However, a drop in sulfur content to 0.38 parts of sulfur/1 part hindered phenol gives significantly more crystallization. A higher sulfur content is expected to improve liquidity but would significantly hurt elastomer seal compatibility and copper corrosion characteristics.

In general terms, the antioxidant compositions of the present invention include antioxidant compositions comprising at least one thiophenol according to the following formula:

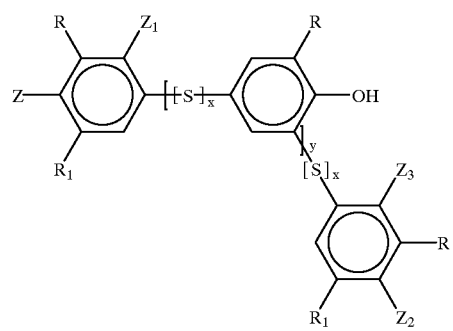

wherein R is an alkyl group; wherein $R_1$ is selected from the group consisting of alkyl groups and hydrogen; wherein one of Z or $Z_1$ is OH with the other being hydrogen; wherein one of $Z_2$ or $Z_3$ is OH with the other being hydrogen; x is in the range of from 1 to 8; and y is in the range of from 0 to 2, and wherein the antioxidant composition is substantially free of chlorine, and wherein the antioxidant composition being in a substantially liquid form.

In broadest terms the invention includes sulfur-bridged phenols referred to as thiophenols prepared in accordance with the general synthetic scheme:

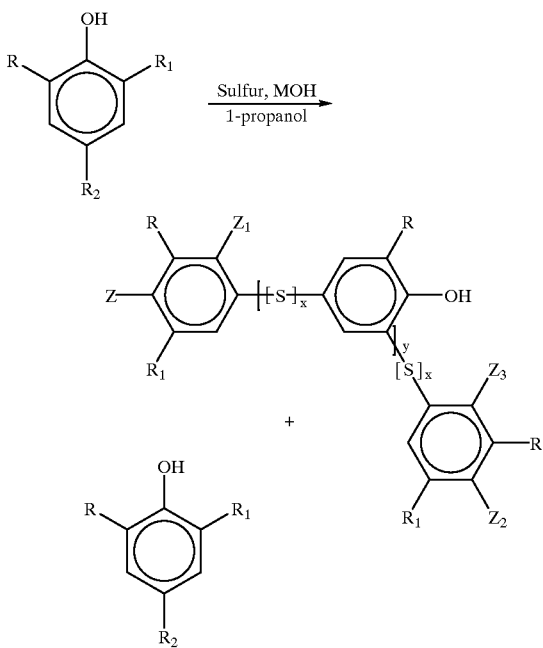

wherein R is an alkyl group; $R_1$ is selected from the group consisting of alkyl groups and hydrogen; $R_2$ is selected from the group consisting of alkyl groups and hydrogen; one of Z or $Z_1$ is OH with the other being hydrogen; one of $Z_2$ or $Z_3$ is OH with the other being hydrogen; x is in the range of from 1 to 8; and y is in the range of from 0 to 2. M may be selected from lithium, sodium, potassium, and cesium.

The main advantage of this invention over that described in U.S. Pat. No. 4,946,610 is the use of a chlorine-free sulfur source and the preparation of a product with less unreacted 2,6-dialkylphenol. A further advantage is that the sulfurized hindered phenol product of the present invention is substantially chlorine-free which leads to improved corrosion properties.

The main advantage of this invention over that described in pending application Ser. No. 08/657,141 is that when 1-propanol is used as the solvent, much higher levels of sulfurized trimeric (y=1) and sulfurized tetrameric (y=2) species are unexpectedly formed. This gives compositions with improved oil solubility and less tendency to crystallize. Other analogous and homologous solvents produce less trimeric and tetrameric components resulting in products with a greater tendency to crystallize and poorer oil solubility. Further, the higher levels of trimeric and tetrameric species produced using 1-propanol allows for the use of less sulfur in the sulfurization process, thus producing a substantially liquid composition with improved corrosion and seal compatibility properties as well as better conversion rates with regard to sulfur.

The present invention also includes lubricating compositions and liquid organic fuels containing a hindered thiophenol additive according to the present invention.

It is preferred that the hindered thiophenol additive be present in the lubricating compositions or the liquid organic fuels in concentrations ranging from 0.005 to 5.0% by weight, preferably 0.01 to 2.0% by weight and most preferably from 0.3 to 2.0% by weight based on the total weight of the compositions.

The lubricating composition and liquid organic fuel of the present invention may additionally comprise at least one composition selected from the group consisting of dispersants, detergents, antiwear additives, supplemental antioxidants, viscosity index improvers, pour point depressants, corrosion inhibitors, rust inhibitors, foam inhibitors, and supplemental friction modifiers, as appropriate to the desired application and as is appreciated in the art. The supplemental antioxidants may include those selected from the group consisting of diphenylamines, alkylated diphenylamines, phenyl-napthylamines, tert-butylphenols, sulfurized alkylphenols, sulfurized olefins, dithiocarbamates, oil soluble copper compounds, and oil soluble molybdenum compounds. It is presently believed that the use of supplemental antioxidants will become more common in the future. Thus, preferred compositions of the present invention include more than one antioxidant in addition to sulfurized hindered phenols of the present invention.

Such lubricating compositions and liquid organic fuels may be formulated in accordance with practices known in the art using the additive of the present invention.

The present invention also includes a method of reducing the oxidative environment in a petroleum composition selected from the group consisting of lubricating compositions and organic fuels, which method comprises adding to the petroleum composition an effective amount of the hindered thiophenol antioxidant composition according to the present invention.

The present invention also includes a method of producing a substantially liquid sulfurized hindered phenol, said method comprising the steps: (a) preparing a mixture of: (i) at least two substantially chlorine-free hindered phenols; (ii) a substantially chlorine-free sulfur source; and (iii) at least one alkali metal hydroxide promoter; in 1-propanol; and (b) causing components (i), (ii) and (iii) to react for sufficient time and at sufficient temperature so as to form at least one chlorine-free sulfurized hindered phenol.

The hindered phenol may be selected from the group consisting of:

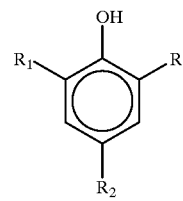

wherein R is selected from the group consisting of alkyl groups; $R_1$ is selected from the group consisting of alkyl groups and hydrogen; and $R_2$ is selected from the group consisting of alkyl groups and hydrogen. It is preferred that the R group and the $R_1$ group be selected from the group consisting of alkyl groups of 3 to 12 carbons and hydrogen, and most preferably from the group consisting of alkyl groups of 4 to 6 carbons and hydrogen.

The hindered phenol may be selected from the group consisting of: 2-t-butylphenol, 2,6-di-t-butylphenol, 2,4-di-t-butylphenol, 2-sec-butylphenol, 2,6-di-sec-butylphenol, 2,4-di-sec-butylphenol, 2-isopropylphenol, 2,6-diisopropylphenol, 2,4-diisopropylphenol, 2-t-octylphenol, 2,6-di-t-octylphenol, 2,4-di-t-octylphenol, 2-cyclopentylphenol, 2,6-dicyclopentylphenol, 2,4-dicyclopentylphenol, 2-t-butyl-p-cresol, 2,6-di-t-amylphenol, 2,4-di-t-amylphenol, 6-t-butyl-o-cresol, 2,6-di-t-dodecylphenol, 2,4-di-t-dodecylphenol, 2-sec-butyl-p-cresol 2,6-di-t-octylphenol, 2,4-di-t-octylphenol, 6-sec-butyl-o-cresol, 2-t-octyl-p-cresol, 2-t-dodecyl-p-cresol, 2-t- butyl-6-isopropylphenol, 6-t-octyl-o-cresol, 6-t-dodecyl-o-cresol, and mixtures thereof, and most preferably will be selected from any two or more such hindered phenols.

It is preferred that the sulfur source comprise elemental sulfur.

The chlorine-free sulfurized hindered phenols of the present invention may be prepared by reacting a hindered phenol mixture with elemental sulfur in the presence of an alkali metal hydroxide promoter and 1-propanol. The reaction is preferably carried out at the reflux temperature of the 1-propanol (approximately 100° C.). A higher reaction temperature will increase the sulfurization yield and the trimer and tetramer content of the product, however, higher temperatures (e.g., 101–120° C.) will often require running the sulfurization reaction under pressure. The process produces alkali metal sulfide waste that may be separated from the product by washing with water. Separation of the aqueous and organic phases may be facilitated by the addition of a non-polar solvent. After the water washes, the non-polar solvent may be removed, yielding the substantially liquid sulfurized hindered phenol product.

The advantages of this process are that the sulfur source is substantially chlorine-free thus producing a chlorine-free sulfurized product. Use of a chlorine-free sulfur source also allows one to drive the reaction further to completion, i.e., reacting greater quantities of hindered phenol, while maintaining a low level of corrosion. It will be understood that reference to the product being substantially chlorine-free is intended to mean that the product is free of amounts of chlorine, in whatever oxidation state, that would cause copper corrosion in a given desired application.

The process thus described produces a composition that is highly sulfurized (typically greater than 6 wt. % sulfur in the final hindered thiophenol product), the main products being sulfur bridged 2,6-dialkylphenols (y=0) and sulfur bridged oligomers (y=1,2) derived from 2,6-dialkylphenols and monoalkylphenols. The number of bridging sulfur atoms between any two bridged phenolic rings can vary from 1 to 8. The process as described produces mostly bridges ranging from one to four sulfurs. Very small quantities of longer chained sulfur bridges, e.g. five, six, and seven, may be produced. Thus, products with low levels of unreacted hindered phenols can be made. An advantage of greater conversions in these reactions is that the products produced are less volatile, a property of practical importance in high temperature lubricant applications.

Another advantage of the process and product of the present invention is that the products are rendered in substantially liquid form which greatly enhances their solubility as an additive, such as when placed in a base oil.

It has also been found that the chlorine-free sulfurized hindered phenol product is an effective antioxidant in both conventional passenger car motor oils, i.e. oils containing approximately 1000 ppm phosphorus derived from ZDDP anti-wear additives, and low phosphorus passenger car motor oils, e.g. oils containing approximately 800 ppm phosphorus derived from ZDDP anti-wear additives.

DETAILED DESCRIPTION OF THE PREFERRED EMBODIMENTS

In accordance with the foregoing summary the following presents a description of the preferred embodiments of the invention, presently considered to be the best mode thereof.

The process described in this invention produces a sulfurized hindered phenol product that has a number of advantages over sulfurized hindered phenols produced using different processes. First, the product produced is substantially liquid with very high solubility in oil. Second, the product is substantially chlorine-free, is compatible with elastomer seals, including but not limited to nitrile rubber seals, and does not cause excessive copper corrosion. Third, the product is a highly effective antioxidant in both conventional motor oils and low phosphorus motor oils as well as liquid organic fuels.

The process for producing this chlorine-free sulfurized hindered phenol involves reacting a hindered phenol mixture with elemental sulfur in the presence of an alkali metal hydroxide promoter and 1-propanol.

The hindered phenolic mixture used in this process should contain at least two different hindered phenols each having at least one hydrogen in the ortho or para position. Hindered phenols of this type are called reactive hindered phenols since at least one ortho or para hydrogen is available in the molecule for reaction with sulfur. By hindered phenol is meant that the phenol is substituted in at least one ortho position with branched chain $C_3$ to $C_{12}$ alkyl groups and preferably a $C_4$ to $C_6$ alkyl group. Examples of suitable ortho-alkylphenols include: 2-t-butylphenol, 2,6-di-t-butylphenol, 2,4-di-t-butylphenol, 2-sec-butylphenol, 2,6-di-sec-butylphenol, 2,4-di-sec-butylphenol, 2-isopropylphenol, 2,6-diisopropylphenol, 2,4-diisopropylphenol, 2-t-octylphenol, 2,6-di-t-octylphenol, 2,4-di-t-octylphenol, 2-cyclopentylphenol, 2,6-dicyclopentylphenol, 2,4-dicyclopentylphenol, 2-t-butyl-p-cresol, 2,6-di-t-amylphenol, 2,4-di-t-amylphenol, 6-t-butyl-o-cresol, 2,6-di-t-dodecylphenol, 2,4-di-t-dodecylphenol, 2-sec-butyl-p-cresol, 2,6-di-t-octylphenol, 2,4-di-t-octylphenol, 6-sec-butyl-o-cresol, 2-t-octyl-p-cresol, 2-t-dodecyl-p-cresol, 2-t-butyl-6-isopropylphenol, 6-t-octyl-o-cresol, 6-t-dodecyl-o-cresol.

Non-reactive hindered phenols may also be present to a minor extent in the hindered phenol mixture. By non-reactive is meant a hindered phenol with no available hydrogens in the ortho or para positions of the phenol. These phenols are completely substituted at the reactive sites of the phenol aromatic ring and are thus not suitable for reaction with sulfur. Examples of such non-reactive hindered phenols include:

| | | |
|---|---|---|
| 2,4,6-tri-t-butylphenol | 4,6-di-t-butyl-o-cresol | 2,6-di-t-butyl-p-cresol |
| 2,4,6-tri-sec-butylphenol | 4,6-di-sec-butyl-o-cresol | 2,6-di-sec-butyl-p-cresol |
| 2,4,6-tri-isopropylphenol | 4,6-diisopropyl-o-cresol | 2,6-diisopropyl-p-cresol |
| 2,4,6-tri-t-amylphenol | 2,4,6-tri-t-octylphenol | 2-t-butyl-6-sec-butyl-p-cresol |

Suitable hindered phenol mixtures contain 75 wt. % to 100 wt. % of a reactive hindered phenolic mixture containing two or more reactive hindered phenols, and from 0 wt. % to 25 wt. % of a non-reactive hindered phenolic mixture containing one or more non-reactive hindered phenols. The mixture preferably contains at least 60 weight % to 99 weight % of a di-ortho branched chain alkylphenol such as 2,6-di-tert-butylphenol, based on the total weight of hindered phenols used in the reaction. Concentrations of ortho-alkylphenol can range from 1 weight % to 30 weight %, preferably 9 weight % to 24 weight %, based on the total weight of hindered phenols used in the reaction. An example of a specific hindered phenolic mixture used in this invention contains 65 wt. % 2,6-di-tert-butylphenol and 22 wt. % ortho-tert-butylphenol as the reactive hindered phenol component, and 11 wt. % 2,4,6-tri-tert-butylphenol as the non-reactive hindered phenolic component.

The hindered phenol mixture may be reacted with elemental sulfur in amounts based on the total reactive hindered phenolic content. Typically, a total of 0.20 to 0.40, preferably 0.28 to 0.38, most preferably 0.32 to 0.36, grams of elemental sulfur are used per gram of hindered phenolics used. Lower levels of sulfur produce less sulfur bridged hindered phenols and/or substantially solid products while higher levels of sulfur produce a more corrosive product. The physical form of the elemental sulfur is not critical.

The alkali metal hydroxide used to promote the reaction may be any of the commercial alkali metal hydroxides, e.g. sodium hydroxide, potassium hydroxide, lithium hydroxide, cesium hydroxide. The amount of alkali metal hydroxide used typically is based on the total amount of hindered phenolics in the mixture. The concentration of alkali metal hydroxide may be in the range of 0.75 to 1.25 molar equivalents of hindered phenolic per molar equivalent of alkali metal hydroxide. Preferably, a molar equivalent of alkali metal hydroxide is used for every molar equivalent of hindered phenolic. For the hindered phenolic mixture described above the alkali metal hydroxide content is determined as follows:

| 2,6-di-t-butylphenol | 65 g/206.36 g/mole | = 0.32 moles |
|---|---|---|
| 2-t-butylphenol | 22 g/150.24 g/mole | = 0.15 moles |
| 2,4,6-tri-t-butylphenol | 11 g/262.48 g/mole | = 0.04 moles |
| Total | | = 0.51 moles phenol |
| Total Alkali Metal Hydroxide Used | | = 0.51 moles sodium hydroxide |
| Sodium Hydroxide | 0.51 moles × 40.0 g/mole | = 20.4 g |

The solvent used in the reaction is 1-propanol. The amount of solvent should be sufficient to dissolve the starting material and solubilize the sulfurized product.

The hindered phenol mixture, elemental sulfur, alkali metal hydroxide, and 1-propanol are combined at room temperature and slowly warmed to reflux temperature. The reaction is carried out at reflux for 30 minutes to 3 hours. The order or rate of addition of the reagents is not critical, and the reaction time and temperature may be varied. After the reaction period the 1-propanol is removed by distillation. Vacuum may be applied in order to facilitate the removal of the last fractions of 1-propanol. The concentrated reaction mixture contains substantial amounts of various alkali metal sulfide salts that may be removed from the product by water washes. Generally, two to three water washes are sufficient to remove the salts with the last water wash containing a small amount of acid. A non-polar solvent may be added during the water washes to facilitate the separation of the organic product from the water phase. Examples of non-polar solvents that may be used include hexane, petroleum ether, ethyl ether, chloroform, methylene chloride, toluene, xylene, benzene, pentane, heptane, and octane. After the last aqueous wash the phases are separated and the organic mixture is concentrated by distillation to give the desired sulfurized hindered phenol product.

The sulfurized liquid hindered phenol product includes, depending upon the phenols in the initial mixture, mixtures of sulfur bridged bisphenols and/or polyphenol compounds such as are represented in the above reaction scheme, where $[S]_x=1$ to 8, R is $C_3$ to $C_{12}$ branched alkyl, $R_1$ and $R_2$ are independently hydrogen or $C_3$ to $C_{12}$ branched alkyl, one of Z or $Z_1$ is OH with the other being hydrogen, one of $Z_2$ or $Z_3$ is OH with the other being hydrogen, and y=0 to 2. The product can also contain 10 to 25 percent of unreacted phenols which contain an ortho or para hydrogen. Of course, the non-reactive hindered phenols originally present in the starting material are unchanged in the reaction and remain in the product.

The sulfurized hindered phenol product typically will be isolated as a high viscosity oil. The product can be used as is or may be diluted in a process or lubricating oil. Typical dilutions contain between 10 wt. % and 95 wt. % of the hindered sulfurized phenolic product with the remainder being one or more mineral or synthetic based lubricants. Typically, dilution is required to facilitate blending in regions where temperatures are low, e.g. arctic regions.

The sulfurized hindered phenol products are added to lubricating compositions or liquid organic fuels in concentrations ranging from 0.005 to 5.0% by weight, preferably 0.01 to 2.0% by weight and most preferably from 0.3 to 2.0% by weight. Typically, the product is added to the oil or fuel in the form of an additive package concentrate. The amount of product in the concentrates generally varies from 0.5 to 50 weight percent or more. The concentrates may also contain other additives.

In automotive crankcase oil applications, the product composition can vary significantly based on the customer and specific application. In general, the crankcase oil is a formulated crankcase oil which is composed of between 75 and 90 wt. % of a mineral lubrication oil, between 0 and 10 wt. % of a polymeric viscosity index improver, and between 8 and 15 wt. % of an additive package. The additive package generally contains the following components:

Dispersants: The dispersants typically are nonmetallic additives containing nitrogen or oxygen polar groups attached to a high molecular weight hydrocarbon chain. The hydrocarbon chain provides solubility in the hydrocarbon base stocks. The dispersants function to keep oil degradation products suspended in the oil. Examples of commonly used dispersants include copolymers such as polymethacrylates and styrenemaleinic ester copolymers, substituted succinamides, polyamine succinamides, polyhydroxy succinic esters, substituted mannich bases, and substituted triazoles. Generally, the dispersant may be present in the finished oil between 4.0 and 8.5% by weight.

Detergents: The detergents typically are metallic additives containing charged polar groups, such as sulfonates or carboxylates, with aliphatic, cycloaliphatic, or alkylaromatic chains, and several metal ions. The detergents function by lifting deposits from the various surfaces of the engine. Examples of commonly used detergents include neutral and overbased alkali and alkaline earth metal sulfonates, neutral and overbased alkali and alkaline earth metal phenates, sulfurized phenates, overbased alkaline earth salicylates, phosphonates, thiopyrophosphonate, and thiophosphonates. Generally, the detergents may be present in the finished oil between 1.0 and 2.5% by weight.

ZDDP's: The ZDDP's (zinc dihydrocarbyl dithiophosphates) typically are the most commonly used antiwear additives in formulated lubricants. These additives function by reacting with the metal surface to form a new surface active compound which itself is deformed and thus protects the original engine surface. Other examples of anti-wear additives include tricresyl phosphate, dilauryl phosphate, sulfurized terpenes and sulfurized fats. The ZDDP's also function as antioxidants. Generally, the ZDDP is present in the finished oil between 1.0 and 1.5 % by weight. It is desirable from environmental concerns to have lower levels of ZDDP.

Antioxidants: Supplemental antioxidants, in addition to the sulfurized hindered phenols of this invention, may be used in oils that are less oxidatively stable or in oils that are subjected to unusually severe conditions. The supplementary antioxidants that are generally used include hindered phenols, hindered bisphenols, sulfurized phenols, alkylated diphenylamines, sulfurized olefins, alkyl sulfides and disulfides, dialkyl dithiocarbamates, phenothiazines, molybdenum compounds and copper salts. The inclusion of the sulfurized hindered phenols of this invention may eliminate the need for some of these supplementary antioxidants.

The lubrication oil component of this invention may be selected from any of the synthetic or natural oils used as lubricants such as that for crankcase lubrication oils for spark-ignited and compression-ignited internal combustion engines, e.g. automobile and truck engines, marine and railroad diesel engines. Synthetic base oils may include alkyl esters of dicarboxylic acids, polyglycols and alcohols, poly-alpha-olefins, including polybutenes, alkyl benzenes, organic esters of phosphoric acids, and polysilicone oils.

Natural base oils include mineral lubrication oils which may vary widely as to their crude source, e.g. as to whether they are paraffinic, naphthenic, or mixed paraffinic-naphthenic.

The lubrication oil base stock conveniently typically will have a viscosity of about 2.5 to about 15 cSt, and preferably about 2.5 to about 11 cSt, at 100° C.

The optional polymeric viscosity index improver (VII) component of this invention may be selected from any of the known viscosity index improvers. The function of the VII is to reduce the rate of change of viscosity with temperature, i.e. they cause minimal increase in engine oil viscosity at low temperature but considerable increase at high temperature. Examples of viscosity index improvers include polyisobutylenes, polymethacrylates, ethylene/propylene copolymers, polyacrylates, styrene/maleic ester copolymers, and hydrogenated styrene/butadiene copolymers.

In addition to the lubricant additives mentioned thus far, there is sometimes a need for other supplemental additives that perform specific functions not provided by the main components. These additional additives include, pour point depressants, corrosion inhibitors, rust inhibitors, foam inhibitors, and supplemental friction modifiers. Again, these additives are not always required but may be used in specific formulations that require them.

There are a number of recent trends in the petroleum additive industry that may restrict and/or limit the use of certain additives in formulated crankcase oils. The key trends are the move to lower phosphorus levels in the oils, the new fuel economy requirements and the move to more severe engine test conditions for qualifying oils. Such changes may show that certain currently used antioxidant additives are no longer effective in protecting the oil against oxidation. The sulfurized hindered phenols disclosed provide a solution to this need. Furthermore, there is concern that phosphorus from the lubricant tends to poison catalyst used in catalytic converters, thereby preventing them from functioning to fill effect.

The following Examples show the unique and unexpected benefit of using 1-propanol in the present invention to produce a sulfurized t-butylphenol product with a high trimer and tetramer content. A higher trimer and tetramer content produces a less volatile and more oil soluble product than analogous material with a lower trimer and tetramer content.

EXAMPLE I

Into a 1.0 liter 4-neck round bottom flask equipped with a mechanical stirrer, a water cooled condenser, a thermometer, and an inlet for adding dry nitrogen, was placed in the following order: 216 g of the reaction solvent, 43.2 g sodium hydroxide, the tert-butyl substituted phenolic mixture as indicated in the Table I, and elemental sulfur as indicated in the Table I. Dry nitrogen was passed through the nitrogen inlet, into the reactor, and out of the reactor through the condenser. Connected to the condenser was a scrubber system to scavenge any hydrogen sulfide gas that might escape the reaction. The scrubber system was composed of the following traps placed in series past the condenser: a blank, 15 wt. % aqueous sodium hydroxide, and bleach. The reaction mixture was slowly heated with stirring to the reflux temperature of the solvent and held at that temperature for 1 hour. After the reaction period the reactor was equipped for distillation and the solvent removed. Distillation was continued until the reaction temperature reached 100 to 108° C. Residual solvent was then removed by vacuum distillation at 100° C. for 30 minutes. Water (215 g) was added to the slurry to dissolve the sodium polysulfide salts produced in the process. The two phase system was stirred at 80° C., the phases allowed to separate, and the bottom aqueous phase removed. The resulting organic product was diluted with 223.4 g of Calsol® 5550 naphthenic process oil from Calumet Lubricants Company, and an additional 215 g of water. The two phase system was again stirred at 80° C., the phases allowed to separate, and the bottom aqueous phase removed. The oil/product mixture was washed one final time at 80° C. with a mixture of water (215 g) and concentrated sulfuric acid (0.12 g). The phases were separated and the bottom aqueous phase was removed. Residual water was removed from the product under vacuum while holding the product temperature at 80° C. The product was then filtered through a pressure filtration apparatus using glass filter pads to collect residual insoluble material. The resulting product was weighed, and analyzed for sulfur content, viscosity at 40° C., and product distribution. A Gel Permeation Chromatography (GPC) method utilizing a U.V. detector was used to analyze the product distribution. It has been found that GPC gives useful information regarding the composition of sulfurized t-butylphenols. Peaks in a GPC trace represent molecular weight and/or molecular volume regions and not individual compounds. However, one can use individual compounds as standards to characterize the various molecular weight regions characteristic of a given sample. This has been done with the product distribution results reported in Table I below. The GPC results are reported in area % and are uncorrected for the presence of the diluent process oil.

The results in Table I show the unique ability of 1-propanol (Sample Nos. 1, 2, 5,6, and 7) to produce a sulfurized t-butylphenol product with a higher oligomer content.

TABLE I

Preparation Of Sulfurized t-butylphenols With Low Sulfur Content and High Oligomer Content - Solvent Study

| Run/Sample # | H-4733 Charge (g) | OTBP Charge (g) | Sulfur Charge (g) | Solvent Type | Yield (g) | Sulfur Content (wt. %) | Visc. (40° C., cSt) | GPC* Tetramer (area %) | GPC* Trimer (area %) | GPC Dimer (area %) | GPC TTBP (area %) | GPC DTBP (area %) | GPC MTBP (area %) |
|---|---|---|---|---|---|---|---|---|---|---|---|---|---|
| 1 | 188.3 | 35.1 | 71 | 1-propanol | 415 | 3 | 174 | 2.2 | 14.1 | 58.9 | 6.1 | 12.2 | 4.8 |
| 2 | 200 | 23.4 | 71 | 1-propanol | 424 | 3 | 92 | 2.3 | 13.2 | 58.3 | 6.2 | 13.2 | 5.1 |
| 3 | 200 | 23.4 | 71 | ethanol | 432 | 3.3 | 274 | 0.3 | 6.5 | 72 | 5.7 | 6.8 | 7.2 |
| 4 | 200 | 23.4 | 71 | 2-propanol | 437 | 3 | 182 | 0.3 | 4.6 | 67.7 | 6 | 9.7 | 10.2 |

TABLE I-continued

Preparation Of Sulfurized t-butylphenols With Low Sulfur Content and High Oligomer Content - Solvent Study

| Run/Sample # | H-4733 Charge (g) | OTBP Charge (g) | Sulfur Charge (g) | Solvent Type | Yield (g) | Sulfur Content (wt. %) | Visc. (40° C., cSt) | GPC* Tetramer (area %) | GPC* Trimer (area %) | GPC Dimer (area %) | GPC TTBP (area %) | GPC DTBP (area %) | GPC MTBP (area %) |
|---|---|---|---|---|---|---|---|---|---|---|---|---|---|
| 5 | 188.3 | 35.1 | 80.6 | 1-propanol | 426 | 3.9 | 219 | 1.7 | 16.9 | 60.4 | 5.6 | 9.3 | 4.8 |
| 6 | 200 | 23.4 | 80.6 | 1-propanol | 425 | 3.7 | 199 | 0.7 | 11.3 | 67.7 | 6 | 9.7 | 3.3 |
| 7 | 211.7 | 11.7 | 80.6 | 1-propanol | 437 | 3.8 | 228 | 0.5 | 9.6 | 70.7 | 6 | 9.1 | 2.6 |
| 8 | 200 | 23.4 | 80.6 | ethanol | 422 | 4 | 321 | 0.3 | 7.2 | 74.5 | 5.4 | 4.8 | 6.5 |
| GPC Std. | | | | | | | | | | 100 | | | |
| GPC Std. | | | | | | | | | | | 100 | | |
| GPC Std. | | | | | | | | | | | | 100 | |
| GPC Std. | | | | | | | | | | | | | 100 |

HiTEC ® 4733 is a mixture of t-butylphenols composed of 75 wt. % 2,6-di-t-butylphenol, 13 wt. % 2,4,6-tri-t-butylphenol, and 10 wt. % o-t-butylphenol which is available from Ethyl Corporation
OTBP is o-tert-butylphenol available from Albemarle Corporation
TTBP represents the tri-tert-butylphenol molecular region
DTBP represents the di-tert-butylphenol molecular region
MTBP represents the mono-tert-butylphenol molecular region
*- Classification based on GPC retention times versus known standards
GPC Dimer Std. is 4,4'-thiobis(2,6-di-t-butylphenol)
GPC TTBP Std. is 2,4,6-tri-t-butylphenol available from Aldrich Chemical Company
GPC DTBP Std. is 2,6-di-tert-butylphenol available from Ethyl Corporation
GPC MTBP Std. is o-tert-butylphenol available from Albemarle Corporation

EXAMPLE II

Reactions in this example were performed in a manner analogous to that described in Example I except that only HiTEC® 4733 (75 wt. % 2,6-di-t-butylphenol, 10 wt. % ortho-t-butylphenol, 13 wt. % 2,4,6-tri-t-butylphenol) was used as the source of t-butylphenols and the amount of sulfur used in the reaction was increased to give a sulfur/phenol ratio of 0.424. The resulting product was analyzed for sulfur content, viscosity at 100° C., and product distribution as defined in example I (GPC Method). Reaction conditions and analytical results are shown in Table II.

The results in Table II clearly show that 1-propanol (Sample No. 9) gives both high overall reaction conversions and products with a high content of trimer and tetramer species. Solvents such as 1-butanol (Sample No. 10), 1-pentanol (Sample No. 11), and isobutyl alcohol (Sample No. 13) give much lower overall conversions than 1-propanol. Ethanol (Sample No. 12) gives high overall reaction conversions but also produces less trimer and tetramer species than 1-propanol.

Upon standing at room temperature the sulfurized t-butylphenols produced with ethanol (Sample No. 12) generate solids due to a high content of dimer species and a low content of trimer and tetramer species. The products produced with 1-propanol (Sample No. 9), on the other hand, do not show signs of solid formation because the dimer content is lower and the trimer and tetramer content is slightly higher. The shift in product distribution to a higher trimer and tetramer content produces a more oil soluble product for use in a broader range of lubricants and at higher treatment levels. Furthermore, the improved oil solubility greatly simplifies handling since a completely liquid product can be transported and transferred without the need for expensive heating capabilities.

TABLE II

Preparation Of Sulfurized t-butylphenols With High Sulfur Content and High Oligomer Content - Solvent Study

| Run # | Solvent Type | Reaction Temp. (° C.) | Sulfur Content (wt. %) | Viscosity (100 C, cSt.) | GPC* Tetramer (area %) | GPC* Trimer (area %) | GPC Dimer (area %) | TTBP (area %) | DTBP (area %) | MTBP (area %) | Conv. By GPC** |
|---|---|---|---|---|---|---|---|---|---|---|---|
| 9 | 1-propanol | 99 | 5.4 | | 0.5 | 10.6 | 74.2 | 5.4 | 6.5 | 1.4 | 85.3 |
| 10 | 1-butanol | 100 | 4.6 | 7.7 | 0.2 | 5.3 | 65.8 | 5.8 | 16.1 | 4.6 | 71.4 |
| 11 | 1-pentanol | 100 | 4.8 | 4.8 | 0.3 | 4.8 | 59.4 | 6.5 | 20.6 | 6 | 64.4 |
| 12 | Ethanol | 85 | 5.3 | 14 | 0.3 | 7.1 | 80.1 | 5.2 | 2.9 | 2.4 | 87.5 |
| 13 | Isobutyl alcohol | 104 | 5.2 | 7.5 | 0.4 | 6.6 | 67.7 | 5.6 | 13.6 | 4 | 74.7 |
| GPC Std. | | | | | | | 100 | | | | |
| GPC Std. | | | | | | | | 100 | | | |
| GPC Std. | | | | | | | | | 100 | | |
| GPC Std. | | | | | | | | | | 100 | |

TTBP represents the tri-tert-butylphenol molecular region
DTBP represents the di-tert-butylphenol molecular region
MTBP represents the mono-tert-butylphenol molecular region
*- Classification based on GPC retention times versus known standards
**- Conversion By GPC is calculated from the sum of the Dimer, Trimer and Tetramer species
GPC Dimer Std. is 4,4'-thiobis(2,6-di-t-butylphenol)
GPC TTBP Std. is 2,4,6-tri-t-butylphenol available from Aldrich Chemical Company
GPC DTBP Std. is 2,6-di-tert-butylphenol available from Ethyl Corporation
GPC MTBP Std. is o-tert-butylphenol available from Albemarle Corporation

EXAMPLE III

The following example shows the improved nitrile seal compatibility of liquid sulfurized tert-butylphenols prepared with a low sulfur content using 1-propanol as the reaction solvent.

Samples of sulfurized tert-butylphenols 1, 2, 5, and 6 from example I above were blended into an SAE grade 15W40 type motor oil as shown in Table III. The only additional antioxidants in these blends were the zinc dialkyldithiophosphate (1.00 to 1.06 wt. % treat level) and the alkylated diphenylamine Naugalube® 680 available from Uniroyal Chemical Company (0.40 to 0.50 wt. % treat level). For comparison, samples of sulfurized tert-butylphenol prepared using the process described in co-pending U.S. application Ser. No. 08/657,141, i.e. 2-propanol as the reaction solvent, were also blended into a similar 15W40 oil. The resulting oils were evaluated for their compatibility with Allison C4 Nitrile Seals which are elastomer based seals known to harden severely in the presence of highly active sulfur. The results are shown in Table III.

crystallization after standing for short periods of time. Also, when compared to the oil blended with an antioxidant that does not contain sulfur (Oil Sample A), one sees a detriment in seal compatibility, i.e. a shift in hardness rating from +3 to +5. It is desirable to have less of a detrimental shift.

Note that oil samples E through T, blended with the low sulfur antioxidants described in this invention, show improved nitrile seal compatibility versus oil samples B through D, which are blended with the higher sulfur content antioxidants of Ser. No. 08/657,141. In some cases higher neat antioxidant treat levels and higher sulfur treat levels can be used and still yield passing hardness ratings. The antioxidants used in oil samples E through T are more compatible with nitrile seals and therefore more useful in crankcase lubricants.

TABLE III

Allison C4 Nitrile Seal Compatibility Of Sulfurized Ter-Butyl Phenols

| Oil Sample | Antioxidant | Sulfur Content Of Antioxidant Sample (Wt. %) | Conc. Of Antioxidant (Wt. %) | Sulfur Added To Oil By Antioxidant (Wt. %) | Approximate Activity Of Antioxidant (Wt. %) | Volume Change Passing Limits (−1.50 to +6.00) | Hardness Change Passing Limits (−5 to +5) |
|---|---|---|---|---|---|---|---|
| A | t-Butylphenols[1] | 0 | 0.9 | 0 | 100 | +1.65 | +3 |
| B | Comparative Sample[2] | 4.17 | 1.2 | 0.050 | 50 | +2.66 | +5 |
| C | Comparative Sample[3] | 10.34 | 0.3 | 0.031 | 100 | +1.96 | +6 |
| D | Comparative Sample[3] | 10.34 | 0.5 | 0.052 | 100 | +2.46 | +7 |
| E | Sample 1 | 2.97 | 0.4 | 0.012 | 46 | +0.84 | +4 |
| F | Sample 1 | 2.97 | 0.8 | 0.024 | 46 | +1.16 | +5 |
| G | Sample 1 | 2.97 | 1.2 | 0.036 | 46 | +1.45 | +5 |
| H | Sample 1 | 2.97 | 1.6 | 0.048 | 46 | +1.63 | +5 |
| I | Sample 2 | 3.01 | 0.4 | 0.012 | 47 | +1.23 | +2 |
| J | Sample 2 | 3.01 | 0.8 | 0.024 | 47 | +1.55 | +3 |
| K | Sample 2 | 3.01 | 1.2 | 0.036 | 47 | +1.83 | +4 |
| L | Sample 2 | 3.01 | 1.6 | 0.048 | 47 | +2.01 | +4 |
| M | Sample 5 | 3.93 | 0.4 | 0.016 | 47 | +1.41 | +6 |
| N | Sample 5 | 3.93 | 0.8 | 0.031 | 47 | +1.70 | +4 |
| O | Sample 5 | 3.93 | 1.2 | 0.047 | 47 | +2.22 | +4 |
| P | Sample 5 | 3.93 | 1.6 | 0.063 | 47 | +2.08 | +6 |
| Q | Sample 6 | 3.70 | 0.4 | 0.015 | 47 | +1.85 | +4 |
| R | Sample 6 | 3.70 | 0.8 | 0.030 | 47 | +2.21 | +3 |
| S | Sample 6 | 3.70 | 1.2 | 0.044 | 47 | +2.56 | +3 |
| T | Sample 6 | 3.70 | 1.6 | 0.059 | 47 | +2.81 | +6 |

[1]HiTEC® 4733, available From Ethyl Corporation, contains 75 wt. % 2,6-di-t-butylphenol, 13 wt. % 2,4,6-tri-t-butylphenol, and 10 wt. % ortho-t-butylphenol.
[2]Prepared as described for Sample B, Example VI in 08/657,141.
[3]Prepared as described for Sample A, Example VI in 08/657,141.

The results in Table III clearly show the detrimental properties of the sulfurized t-butylphenols prepared using the process described in Ser. No. 08/657,141. Note that the oils containing antioxidants with a high sulfur content, prepared using the process described in Ser. No. 08/657,141 (Oil Samples C and D), fall outside the passing limits for the hardness rating in this seal compatibility test. Even the oil sample containing a relatively low antioxidant treat level of 0.3 wt. % (Oil Sample C) fails for the hardness rating. These antioxidants are liquids but are not compatible with nitrile seals and therefore have limited applications in crankcase lubricants. An oil containing an antioxidant with a lower sulfur content, prepared using the process described in Ser. No. 08/657,141 (Oil Sample B), shows a borderline pass for the hardness rating in this seal compatibility test. However, the antioxidant used in oil sample B is highly crystalline and is therefore likely to cause handling problems in use. Even 50 wt. % oil dilutions of this sample have shown heavy This invention is susceptible to considerable variation in its practice. Accordingly, this invention is not limited to the specific exemplifications set forth hereinabove. Rather, this invention is within the spirit and scope of the appended claims, including the equivalents thereof available as a matter of law.

The patentee does not intend to dedicate any disclosed embodiments to the public, and to the extent any disclosed modifications or alterations may not literally fall within the scope of the claims, they are considered to be part of the invention under the doctrine of equivalents.

What is claimed is:

1. An antioxidant composition comprising at least one thiophenol of the formula:

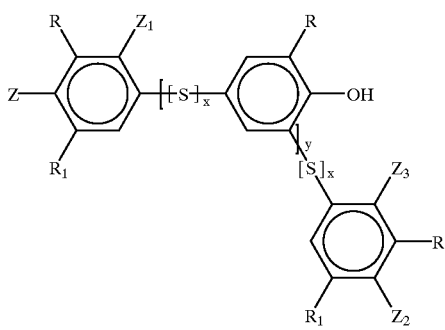

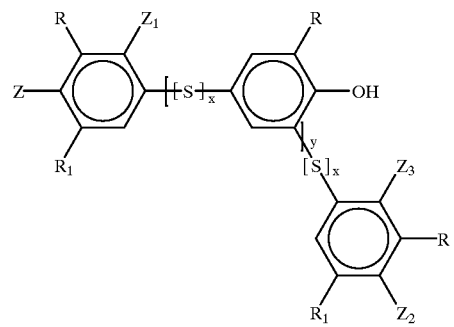

wherein R is an alkyl group; wherein $R_1$ is selected from the group consisting of alkyl groups and hydrogen; wherein one of Z or $Z_1$ is OH with the other being hydrogen; wherein one of $Z_2$ or $Z_3$ is OH with the other being hydrogen; wherein x is in the range of from 1 to 8; and wherein y is in the range of from 0 to 2 and has an average value of greater than 0 for the total antioxidant composition, and said antioxidant composition being in a substantially liquid form, wherein said antioxidant is prepared by a process comprising (a) preparing a mixture of:
  (i) at least two different chlorine-free hindered phenols, wherein said phenols comprise a mixture of at least one dialkyl substituted phenol and at least one monoalkyl substituted phenol;
  (ii) a chlorine-free sulfur source; and
  (iii) at least one alkali metal hydroxide promoter;
  in 1-propanol; and (b) causing components (i), (ii) and (iii) to react for sufficient time and at sufficient temperature so as to form at least one chlorine-free sulfurized hindered phenol.

2. An antioxidant composition according to claim 1 wherein said R group is selected from the group consisting of alkyl groups of 3 to 12 carbons.

3. An antioxidant composition according to claim 1 wherein said $R_1$ group is selected from the group consisting of alkyl groups of 3 to 12 carbons and hydrogen.

4. An antioxidant composition according to claim 1 wherein said R group is selected from the group consisting of alkyl groups of 4 to 6 carbons.

5. An antioxidant composition according to claim 1 wherein said $R_1$ group is selected from the group consisting of alkyl groups of 4 to 6 carbons and hydrogen.

6. An additive composition comprising:
  (a) from about 30% to about 95% by weight of an antioxidant composition comprising at least one thiophenol according to the formula:

wherein R is an alkyl group; wherein $R_1$ is selected from the group consisting of alkyl groups and hydrogen; wherein one of Z or $Z_1$ is OH with the other being hydrogen; wherein one of $Z_2$ or $Z_3$ is OH with the other being hydrogen; wherein x is in the range of from 1 to 8; and wherein y is in the range of from 0 to 2 and has an average value of greater than 0 for the total antioxidant composition, said antioxidant composition being in a substantially liquid form, wherein said antioxidant composition is prepared by a process comprising (a) preparing a mixture of:
  (i) at least two different chlorine-free hindered phenols, wherein said phenols comprise a mixture of at least one dialkyl substituted phenol and at least one monoalkyl substituted phenol;
  (ii) a chlorine-free sulfur source; and
  (iii) at least one alkali metal hydroxide promoter;
  in 1-propanol; and (b) causing components (i), (ii) and (iii) to react for sufficient time and at sufficient temperature so as to form at least one chlorine-free sulfurized hindered phenol; and (c) the balance of said additive comprising at least one mineral or synthetic lubricant oil.

7. A lubricating composition containing an antioxidant composition according to claim 1.

8. A lubricating composition according to claim 7 wherein said antioxidant composition is present in said lubricating composition at a concentration in the range of from 0.005% to about 5.0% by weight.

9. A lubricating composition according to claim 7 wherein said antioxidant composition is present in said lubricating composition at a concentration in the range of from 0.3% to about 2.0% by weight.

10. A lubricating composition according to claim 7, said lubricating composition additionally comprising at least one composition selected from the group consisting of dispersants, detergents, antiwear additives, supplemental antioxidants, viscosity index improvers, pour point depressants, corrosion inhibitors, rust inhibitors, foam inhibitors, and supplemental friction modifiers.

11. A lubricating composition according to claim 10, wherein said supplemental antioxidants are selected from the group consisting of diphenylamines, alkylated diphenylamines, phenyl-napthylamines, tert-butylphenols, sulfurized alkylphenols, sulfurized olefins, dithiocarbamates, oil soluble copper compounds, and oil soluble molybdenum compounds.

12. An organic fuel containing an antioxidant composition according to claim 1.

13. An organic fuel according to claim 12 wherein said antioxidant composition is present in said liquid organic fuel at a concentration in the range of from 0.005% to about 5.0% by weight.

14. An organic fuel according to claim 12 wherein said antioxidant composition is present in said liquid organic fuel at a concentration in the range of from 0.01 to about 2.0% by weight.

15. A method of producing a substantially liquid sulfurized hindered phenol, said method comprising the steps:
   (a) preparing a mixture of:
      (i) at least two different chlorine-free hindered phenols, wherein said phenols comprise a mixture of at least one dialkyl substituted phenol and at least one monoalkyl substituted phenol;
      (ii) a chlorine-free sulfur source; and
      (iii) at least one alkali metal hydroxide promoter;
      in 1-propanol; and
   (b) causing components (i), (ii) and (iii) to react for sufficient time and at sufficient temperature so as to form at least one chlorine-free sulfurized hindered phenol.

16. A method according to claim 15 wherein said at least two hindered phenols are selected from the group consisting of:

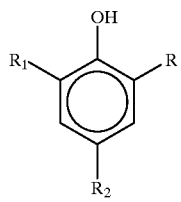

wherein R is an alkyl group; $R_1$ is selected from the group consisting of alkyl groups and hydrogen; and $R_2$ is selected from the group consisting of alkyl groups and hydrogen.

17. A method according to claim 16 wherein said R group is selected from the group consisting of alkyl groups of 3 to 12 carbons.

18. A method according to claim 16 wherein said $R_1$ group is selected from the group consisting of alkyl groups of 3 to 12 carbons and hydrogen.

19. A method according to claim 16 wherein said R group is selected from the group consisting of alkyl groups of 4 to 6 carbons.

20. A method according to claim 16 wherein said $R_1$ group is selected from the group consisting of alkyl groups of 4 to 6 carbons and hydrogen.

21. A method according to claim 15 wherein said at least two liquid hindered phenols are selected from the group consisting of: 2-t-butylphenol, 2,6-di-t-butylphenol, 2,4-di-t-butylphenol, 2-sec-butylphenol, 2,6-di-sec-butylphenol, 2,4-di-sec-butylphenol, 2-isopropylphenol, 2,6-diisopropylphenol, 2,4-diisopropylphenol, 2-t-octylphenol, 2,6-di-t-octylphenol, 2,4-di-t-octylphenol, 2-cyclopentylphenol, 2,6-dicyclopentylphenol, 2,4-dicyclopentylphenol, 2-t-butyl-p-cresol, 2,6-di-t-amylphenol, 2,4-di-t-amylphenol, 6-t-butyl-o-cresol, 2,6-di-t-dodecylphenol, 2,4-di-t-dodecylphenol, 2-sec-butyl-p-cresol 2,6-di-t-octylphenol, 2,4-di-t-octylphenol, 6-sec-butyl-o-cresol, 2-t-octyl-p-cresol, 2-t-dodecyl-p-cresol, 2-t-butyl-6-isopropylphenol, 6-t-octyl-o-cresol, 6-t-dodecyl-o-cresol, and mixtures thereof.

22. A method according to claim 15 wherein said at least one sulfur source comprises elemental sulfur.

23. A method of reducing the oxidative environment in a petroleum composition selected from the group consisting of lubricating compositions and liquid organic fuels, said method comprising adding to said petroleum composition an effective amount of an antioxidant composition comprising at least one thiophenol according to the following formula:

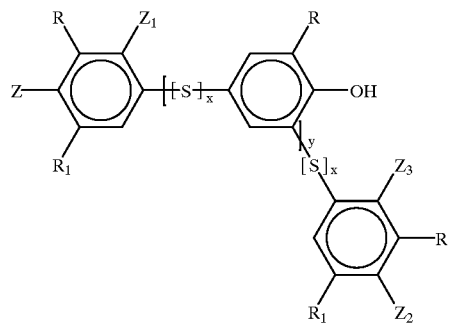

wherein R is an alkyl group; wherein $R_1$ is selected from the group consisting of alkyl groups and hydrogen; wherein one of Z or $Z_1$ is OH with the other being hydrogen; wherein one of $Z_2$ or $Z_3$ is OH with the other being hydrogen; wherein x is in the range of from 1 to 8; and y is in the range of from 0 to 2 and has an average value of greater than 0 for the total antioxidant composition and said antioxidant composition being in a substantially liquid form, and wherein said antioxidant is prepared by a process comprising
   (a) preparing a mixture of:
      (i) at least two different chlorine-free hindered phenols, wherein said phenols comprise a mixture of at least one dialkyl substituted phenol and at least one monoalkyl substituted phenol;
      (ii) a chlorine-free sulfur source; and
      (iii) at least one alkali metal hydroxide promoter;
      in 1-propanol; and
   (b) causing components (i), (ii) and (iii) to react for sufficient time and at sufficient temperature so as to form at least one chlorine-free sulfurized hindered phenol.

24. A method according to claim 23 wherein said R group is selected from the group consisting of alkyl groups of 3 to 12 carbons.

25. A method according to claim 23 wherein said $R_1$ group is selected from the group consisting of alkyl groups of 3 to 12 carbons and hydrogen.

26. A method according to claim 23 wherein said R group is selected from the group consisting of alkyl groups of 4 to 6 carbons.

27. A method according to claim 23 wherein said $R_1$ group is selected from the group consisting of alkyl groups of 4 to 6 carbons and hydrogen.

28. A method according to claim 23 wherein said antioxidant composition is present in said petroleum composition at a concentration in the range of from 0.05% to about 5.0% by weight.

29. A method according to claim 23 wherein said antioxidant composition is present in said petroleum composition at a concentration in the range of from 0.5% to about 2.0% by weight.

30. An improved antioxidant composition comprising at least one thiophenol of the formula:

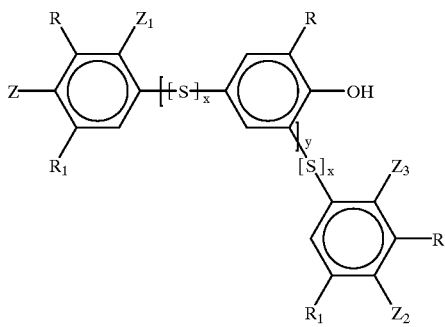

wherein R is an alkyl group; wherein $R_1$ is selected from the group consisting of alkyl groups and hydrogen; wherein one of Z or $Z_1$ is OH with the other being hydrogen; wherein one of $Z_2$ or $Z_3$ is OH with the other being hydrogen; wherein x is in the range of from 1 to 8; and wherein y is in the range of from 0 to 2 and has an average value of greater than 0 for the total antioxidant composition and said antioxidant composition being in a substantially liquid form, wherein said antioxidant is prepared by an improved process comprising (a) preparing a mixture of:
   (i) at least two different chlorine-free hindered phenols, wherein said phenols comprise a mixture of at least one dialkyl substituted phenol and at least one monoalkyl substituted phenol;
   (ii) a chlorine-free sulfur source; and
   (iii) at least one alkali metal hydroxide promoter;
   in an organic solvent; and (b) causing components (i), (ii) and (iii) to react for sufficient time and at sufficient temperature so as to form at least one chlorine-free sulfurized hindered phenol, wherein the improvement comprises using 1-propanol as the organic solvent.

* * * * *